United States Patent [19]

Senaratne et al.

[11] Patent Number: 5,322,633
[45] Date of Patent: Jun. 21, 1994

[54] PREPARATION OF BRANCHED CHAIN CARBOXYLIC ESTERS

[75] Inventors: K. Pushpananda A. Senaratne; Kenneth C. Lilje, both of Baton Rouge, La.

[73] Assignee: Albemarle Corporation, Richmond, Va.

[21] Appl. No.: 976,817

[22] Filed: Nov. 16, 1992

[51] Int. Cl.$^5$ .................................. C10M 129/70
[52] U.S. Cl. ............................ 252/56 R; 560/243; 252/56 S
[58] Field of Search ............... 252/56 S, 56 R; 560/243

[56] References Cited

U.S. PATENT DOCUMENTS

| | | | |
|---|---|---|---|
| 2,964,558 | 12/1960 | Leathers et al. | 560/206 |
| 3,060,228 | 10/1962 | Pino | 560/206 |
| 3,334,132 | 8/1967 | Landis | 560/206 |
| 3,471,532 | 10/1969 | Young | 560/243 |
| 4,167,486 | 9/1979 | Rowe | 252/56 R |
| 4,313,893 | 2/1982 | Pesa | 560/243 |
| 4,658,053 | 4/1987 | Green | 560/234 |
| 4,769,498 | 9/1988 | Billig et al. | 568/454 |
| 4,900,462 | 2/1990 | Haag et al. | 252/52 R |

OTHER PUBLICATIONS

Kirk Othmer, Encyclopedia of Chemical Technology, Third Edition, vol. 4, pp. 805-806 (1978).

*Primary Examiner*—Jacqueline V. Howard
*Attorney, Agent, or Firm*—David M. Bunnell

[57] ABSTRACT

Branched chain carboxylic esters are prepared by reacting an unsaturated PAO such as 1-decene dimer with CO and an aliphatic alcohol solvent in the presence of an acid and a noble metal catalyst complex such as RuCl$_3$/Ph$_3$P or PdCl$_3$/Ph$_3$P.

18 Claims, No Drawings

PREPARATION OF BRANCHED CHAIN CARBOXYLIC ESTERS

This invention relates generally to functionalized polyalphaolefin oligomers useful in lubricant applications and more particularly to unsaturated polyalphaolefin oligomers which have been reacted with carbon monoxide gas in alcohol solution to form branched chain carboxylic esters.

Alpha-olefin oligomers (PAO's) derived from $C_6$ or higher alpha-olefin monomer and their use as functional fluids and synthetic lubricants are well known. Such oligomers are usually hydrogenated to improve their oxidation resistance and are known for their superior properties of long-life, low volatility, low pour points and high viscosity indices which make them a premier basestock for state-of-the-art lubricants and hydraulic fluids. A problem associated with such basestocks is that polar lubricant additives are generally less soluble in PAO's than in mineral oils and the PAO's do not swell rubber seals. PAO's have been reacted with compounds which contain polar groups, such as phenols, in order to improve their compatibility with polar additives but such compounds still require the addition of seal swell agents such as certain esters.

PAO's manufactured using Friedel-Crafts catalysts, such as $BF_3$ promoted with water or alcohols, are highly branched internal olefins. The hindered nature of the double bonds can make them less reactive. We have now provided a process whereby such materials can be carboxylated in good yield to provide branched chain carboxylic esters which are useful as seal swell agents and solubilizers and are compatible when mixed with synthetic lubricants in additive quantities.

In accordance with this invention there are provided branched chain carboxylic esters prepared by the process comprising reacting a branched chain unsaturated olefin oligomer derived from an alpha-olefin monomer containing from about 6 to 20 carbon atoms with CO in an $C_1$ to $C_4$ aliphatic alcohol solvent in the presence of a noble metal catalyst and an acid.

Also provided is a process for preparing branched chain carboxylic esters which process comprises reacting a branched chain unsaturated olefin oligomer derived from an alpha-olefin monomer containing from about 6 to 20 carbon atoms with CO in a $C_1$ to $C_4$ aliphatic alcohol solvent in the presence of a noble metal catalyst and an acid.

Also provided are lubricant compositions containing the branched chain carboxylic esters.

The preparation of alpha-olefin oligomers is well known. For example, U.S. Pat. No. 3,113,167 describes an alpha-olefin oligomer process using a titanium halide and an aluminum compound as the oligomerization catalyst.

Other suitable catalysts for making alpha-olefin oligomers are Friedel-Crafts catalysts such as boron trifluoride ($BF_3$) as disclosed in U.S. Pat. No. 3,149,176. Optimum lubricant properties are obtained starting with 1-decene although mixtures of alpha-olefins have been used cf. U.S. Pat. No. 3,330,883. Pure $BF_3$ is not an effective oligomerization catalyst. A small amount of polar compound is necessary as a promoter. U.S. Pat. No. 3,382,291 describes the use of alcohol promoters such as decanol. Alcohols containing about 1-8 carbon atoms such as methanol, ethanol, isopropanol, n-propanol, n-butanol, isobutanol, n-hexanol and n-octanol can also be used. A preferred promoter is n-butanol. Other promoters include, for example, mordenite (hydrogen form), water, phosphoric acid, fatty acids (e.g. valeric acid), aldehydes, ketones, organic esters, ethers, polyhydric alcohols, silica gel and the like.

The amount of promoter is an amount that causes the $BF_3$ to act as an oligomerization catalyst. A useful range is about 0.1 to 2.0 weight percent of the alpha-olefin.

Methods of conducting a $BF_3$ catalyzed oligomerization process are well-known. In one mode, $BF_3$ is merely bubbled through the alpha-olefin reaction mixture containing a promoter during the oligomerization. Generally, the process is conducted under $BF_3$ pressure. A useful pressure is about 1-100 psig and especially 5-50 psig.

Alpha-olefins most useful in preparing synthetic lubricant oils are mainly linear terminal olefins containing about 8-12 carbon atoms such as 1-octene, 1-decene, 1-dodecene and the like including mixtures thereof. The most preferred alpha-olefin is 1-decene or an olefin mixture containing mainly, for example, at least 75 weight percent 1-decene.

Generally, reaction temperatures are about 20°-50° C. and especially about 25°-40° C.

The oligomer products are mixtures which include varying amounts of dimer, trimer, tetramer, pentamer and higher oligomers of the monomer, depending upon the particular alpha-olefin, catalyst and reaction conditions. The products are unsaturated and usually have kinematic viscosities ranging from about 2 to 12 cSt at 100° C., a molecular weight range of 100 to 1000 and a molecular weight distribution (ratio of weight average molecular weight to number average molecular weight) of 1.02 to 1.04.

The oligomers prepared using Friedel-Crafts catalysts are branched materials which contain more than the expected number of branches due to isomerization or rearrangement which occurs during oligomerization. This additional branching can be expressed as the excess methyl ratio. An oligomer material with little or no excess branching such as is described in U.S. Pat. No. 4,827,064 would have an excess methyl ratio of $<1.05$ or close to 1.00 The oligomers prepared using Friedel-Crafts catalysts would have excess methyl ratios of 1.05 or above and especially from 1.05 to 1.20. The ratio is determined by calculating the ratio of experimentally determined methyls/molecule to a calculated theoretical methyls/molecule (assuming no excess branching in the theoretical case).

Excess Methyl Ratio = (experimental methyls/molecule) ÷ (calculated methyls/molecule).

(a) Experimental Methyls/Molecule: This number is determined by NMR spectroscopy. A 300 MHz instrument is used to determine the integral for methyl groups (X) and the integral for total protons (Y). Also used in the calculation is the "theoretical" number of protons (N). This number (N) is calculated from the GC determined oligomer distribution. With these values, the methyls/molecule value is calculated using the following equation:

$$Methyls/molecule = X/3 \div Y/N$$

(b) Calculated, Theoretical Methyls/Molecule: This value is calculated assuming all oligomers are "head to tail" and that no isomerization or rearrangement occurs. The theoretical value is one more than the oligomer number. Thus dimer has 3 methyls/molecule, trimer has 4, etc. In a mixture of oligomers the sum of the wt fraction of theoretical methyls for each oligomer is the theoretical value. Thus a 1:1 mixture of dimer and trimer would give:

$$0.5(3) + 0.5(4) = 3.5 \text{ methyls/molecule}$$

Preferred oligomer products for use in preparing the branched chain esters of the invention contain from about 12 to 96 carbon atoms with 80 weight % $\leq C_{54}$, most preferred are dimers of 1-decene ($C_{20}H_{40}$). The starting unsaturated PAO oligomer is a complex mixture of isomers. Tri-substituted olefins constitute the bulk of this mixture @$\geq$70 mole % and $\leq$20 mole % vinylidene olefins in contrast to the oligomers prepared in accordance with U.S. Pat. No. 4,827,064 which are mainly $\leq$90 mole % vinylidene olefins and $\leq$10% tri-substituted olefins. Generally, carbonylations of tri-substituted olefins are difficult relative to unbranched olefins.

A typical branched chain 1-decene dimer product, as analyzed by high field proton NMR (e.g. 300 MHz), has the following distribution of olefins.

|  | α | Internal | Vinylidene | Trisubstituted |
|---|---|---|---|---|
| $C_{20}$ | 0 | 18.0 (RCH=CHR) | 10.0 ($R_2C$=$CH_2$) | 71.0 (RCH=$CR_2$) |

It is well known that high field NMR (e.g. 300 MHz) can be used to distinguish different types of olefinic protons. This allows one to calculate normalized mole % of olefin types (e.g. vinylidene, internal, alpha and trisubstituted) for complex mixtures.

The branch ratios of the oligomer products of the Friedel-Crafts catalyzed oligomerization, calculated according to the formula:

$$\text{Branch ratio} = \frac{\text{(weight fraction of methyl groups)}}{1 - \text{(weight fraction of methyl groups)}}$$

are $\geq$0.2 and usually about 0.2 to 0.4. The weight fraction of methyl groups is determined according to the procedure described in *Analytical Chemistry*, Vol. 25, No. 10, p. 1466 (1953).

According to the process of the invention, the oligomer is dissolved in a $C_1$ to $C_4$ aliphatic alcohol solvent in proportions of from about 0.05 to 1 mole of oligomer per mole of solvent. Non-limiting examples of alcohols for use in the invention are methanol, ethanol, propanol, n-butanol, and the like.

Suitable catalysts are complexes of noble metal halides with hydrocarbyl phosphine. Suitable catalysts can be represented by the formula $MX_3/R_3P$, where M is a noble metal selected from Pd, Ru, and Rh, X is halogen (Br, Cl, F, I) and each R is independently a $C_1$ to about $C_{20}$ hydrocarbyl group. Non-limiting examples of noble metal halides are $PdCl_3$, $RuCl_3$, $RhCl_3$ and the like. Non-limiting examples of hydrocarbyl (alkyl, aryl or mixed alkylaryl phosphines are triphenylphosphine, trimethylphosphine, triethylphosphine, ethyldiphenylphosphine and the like. The catalyst complexes are used in amounts which are effective to catalyze the reaction. Preferably, from about $7 \times 10^{-3}$ to $10 \times 10^{-3}$ moles of catalyst per mole of oligomer are used.

The reaction is carried out under CO pressure at temperatures of from about 80° to 150° C. and preferably from about 80° to 110° C. CO pressures of from about 1000 to 3000 psig can be used and preferably from about 1500 to 2000 psig.

The reaction is carried out in an acidic medium provided by adding an acid to the reaction mixture to provide an acid concentration of from about 2.5 to 5.0% . Preferred acids are inorganic (mineral) acids and especially HCl.

The branched chain carboxylic ester can be used as a base fluid either by itself or in blends with mineral oils or other synthetic oils (polyolefin oils, synthetic esters, etc.). The ester can also be used as an additive in various lubricant and functional fluid applications such as, for example, 2-stroke oils, crankcase oils, transmission fluids, compressor oils, turbine oils, hydraulic fluids, brake fluids, metalworking fluids, gear oils, greases, shock absorber fluids, heat transfer fluids, transformer oils, oil or water base drilling fluids, and the like as well as other typical applications for long chain esters such as additives for plastics, paints, coatings, elastomers, cosmetics and personal hygiene products (e.g. soaps, lotions, lipsticks, creams, antiperspirants, etc.) The PAO derived branched chain esters are expected to have, besides excellent seal swell properties, enhanced properties with respect to lubricity, antiwear, biodegradability, thermal and oxidative stability and detergency.

The branched chain carboxylic esters can be used in additive quantities of about 0.1 to 25 wt. percent, based on the total weight composition, in polyalphaolefin synthetic base fluids to provide the fluids with the necessary seal swell properties and to solubilize other lubricant oil additives. The products have unexpectedly superior seal swell properties when compared to the commercial ester seal swell agent, ditridecyl adipate. The branched chain esters can also be used as additives in conjunction with mineral oils or other ester fluids to impart improved properties such as dispersivity, compatibility, biodegradability, etc. to the base fluids. They can be added directly to the base oil or incorporated into standard lubricant additive packages which contain other lubricant additives such as dispersants, anti-wear agents, friction reducers, viscosity index improvers, anti-oxidants, corrosion inhibitors, detergents, foam inhibitors and the like. The additive packages are mixed with the polyalphaolefin or other base oils to provide the finished lubricants.

The invention is further illustrated by, but is not limited to, the following examples.

EXAMPLE 1

A solution of 50 gms (0.178 moles) of unsaturated PAO (a 1-decene dimer having a 100° C. kinematic viscosity of 2 cSt) in 50 ml of n-BuOH (0.546 moles) was charged into a Hastaloy autoclave with 0.3 gms (0.0015 mols) of $PdCl_2$, 0.4 gms (0.0016 mols) of $Ph_3P$ and 20 ml of aqueous HCl (18%). The autoclave was pressurized with CO gas to 500 psig and heated to 100° C. Upon reaching this temperature, the internal pressure of the reactor was increased to 2000 psig with more CO and the reaction mixture was stirred for 24 hrs. The contents were cooled and washed with water (2×200 ml), the orqanic layer was dried over anhydrous $MgSO_4$, filtered and passed through a short column packed with Florisil. According to gas chromatography (GC) the conversion of olefin was 25%. GC/MS, m/e 382; FTIR (Film) 1736(s).

EXAMPLE 2

The process conducted was the same as Example 1, except that RuCl$_3$ was used instead of PdCl$_2$ and the reaction temperature was lowered to 85° C. According to GC analysis the conversion of olefin to product was 27%.

EXAMPLE 3

A solution of 50 gms (0.178 mols) of unsaturated 1-decene dimer with a 100° C. viscosity of 2 cSt) in 50 ml of n-butanol (0.546 mols) was charged into a Hastaloy autoclave with 0.3 gms (0.0015 mols) of Ph$_3$P, 0.118 gms (0.0005 mols) of RuCl$_3$ and 20 ml of aqueous HCl (18%). The autoclave was pressurized with CO gas to 500 psig and heated to 100° C. The internal pressure was increased to 2000 psig with more CO and the reaction mixture was stirred for 48 hours. The contents were cooled and washed with water (2×200 ml), the organic layer was dried over anhydrous MgSO$_4$, filtered and passed through a short column of Florisil. According to GC analysis the conversion of olefin was 75%.

The carboxylated PAO product of the invention was tested as a seal swell agent in a commercial lube additive package HCE 5W50. A commercial ester seal-swell agent ditridecyl adipate (DTDA) was used as the standard. The PAO ester and DTDA were added at 5% by weight to HCE 5W50 and heated to 150° C. for 70 hrs. with the respective seal material and the volume changes were recorded. The results are summarized as follows:

|  | Seal Material Volume Change in (%) | | |
| --- | --- | --- | --- |
|  | Viton | Polyacrylic Rubber | Buna Nitrile |
| HCE 5W50 + DIDA | 0.3 | 1.1 | −1.2 |
| HCE 5W50 + (No Additive) | −1.3 | 0.2 | −3.2 |
| HCE 5W50 + PAO-ester | 2.5 | 2.3 | 4.5 |

This demonstrates that the PAO-esters of the invention provided unpredictably greater seal swell than DTDA. This has the advantages of requiring less seal swell agent to obtain the same seal swell effect which in turn reduces the impact of the seal swell agent on the other properties of the lubricant additive package since the amount of agent needed is smaller.

We claim:

1. Branched chain carboxylic ester prepared by the carbonylation process comprising reacting a branched chain unsaturated olefin oligomer, derived from an alpha-olefin monomer containing from about 6 to 20 carbon atoms, with a reactant gas consisting essentially of CO in a C$_1$ to C$_4$ aliphatic alcohol solvent in the presence of a noble metal catalyst and an inorganic acid, wherein the reaction pressure is from about 1,000 to 3,000 psig and the reaction temperature is from about 80° to 150° C.

2. The ester according to claim 1 wherein the catalyst is represented by the formula MX$_3$/R$_3$P, where M is a noble metal selected from Pd, Ru and Rh, X is halogen, and each R is independently a C$_1$ to C$_{20}$ hydrocarbyl group, and the acid is HCl.

3. The ester according to claim 2 wherein said oligomer contains from about 20 to 40 carbon atoms and said oligomer has a branch chain ratio of $\geq 0.2$.

4. The ester according to claim 3 wherein said oligomer is a dimer of 1-decene and the branch chain ratio is from about 0.2 to 0.4.

5. The ester according to claim 2 wherein from about $7 \times 10^{-3}$ to $10 \times 10^{-3}$ moles of catalyst per mole of oligomer is used.

6. The ester according to claim 5 wherein the aliphatic alcohol solvent is n-butanol and forms the alcohol portion of said ester.

7. A carbonylation process for preparing a branched chain carboxylic ester, which process comprises reacting a branched chain unsaturated olefin oligomer, derived from an alpha-olefin monomer containing from about 6 to 20 carbon atoms, with a reactant gas consisting essentially of CO in a C$_1$ to C$_4$ aliphatic alcohol solvent in the presence of a noble metal catalyst and an inorganic acid, wherein the reaction pressure is from about 1,000 to 3,000 psig and the reaction temperature is from about 80° to 150° C.

8. The process according to claim 7 wherein the catalyst is represented by the formula MX$_3$/R$_3$P, where M is a noble metal selected from Pd, Ru and Rh, X is halogen, and each R is independently a C$_1$ to C$_{20}$ hydrocarbyl group, and the acid is HCl.

9. The process according to claim 8 wherein said oligomer contains from about 20 to 40 carbon atoms and said oligomer has a branch chain ratio of $\geq 0.2$.

10. The process according to claim 9 wherein said oligomer is a dimer of 1-decene.

11. The process according to claim 8 wherein from about $7 \times 10^{-3}$ to $10 \times 10^{-3}$ moles of catalyst per mole of oligomer is used.

12. The process according to claim 11 wherein the aliphatic alcohol solvent is n-butanol.

13. A lubricant composition comprising a base oil and from about 0.1 to 25 wt. percent of composition of a branched chain carboxylic ester prepared by the carbonylation process comprising reacting a branched chain unsaturated olefin oligomer, derived from an alpha-olefin monomer containing from about 6 to 20 carbon atoms, with a reactant gas consisting essentially of CO in a C$_1$ to C$_4$ aliphatic alcohol solvent in the presence of a noble metal catalyst and an inorganic acid, wherein the reaction pressure is from about 1,000 to 3,000 psig and the reaction temperature is from about 80° to 150° C.

14. The lubricant composition of claim 13 wherein said base oil is selected from the group consisting of mineral oil, synthetic polyolefin oil, synthetic ester oil and mixtures thereof.

15. The lubricant composition of claim 13 wherein said base oil is a synthetic polyolefin oil.

16. The lubricant composition of claim 13 wherein said base oil is a synthetic polyalphaolefin oil.

17. The lubricant composition of claim 13 wherein said base oil is mineral oil.

18. A lubricant composition comprising (a) a base oil which comprises a branched chain carboxylic ester prepared by the carbonylation process comprising reacting a branched chain unsaturated olefin oligomer, derived from an alpha-olefin monomer containing from about 6 to 20 carbon atoms, with a reactant gas consisting essentially of CO in a C$_1$ to C$_4$ aliphatic alcohol solvent in the presence of a noble metal catalyst and an inorganic acid, wherein the reaction pressure is from about 1,000 to 3,000 psig and the reaction temperature is from about 80° to 15° C., and (b) at least one lubricant additive.

* * * * *